United States Patent
Nisani

(10) Patent No.: US 10,143,400 B2
(45) Date of Patent: Dec. 4, 2018

(54) IN-VIVO DEVICE USING TWO COMMUNICATION MODES

(71) Applicant: GIVEN IMAGING LTD., Yoqneam (IL)

(72) Inventor: Micha Nisani, Nesher (IL)

(73) Assignee: GIVEN IMAGING LTD., Yoqneam (IL)

( * ) Notice: Subject to any disclaimer, the term of this patent is extended or adjusted under 35 U.S.C. 154(b) by 177 days.

(21) Appl. No.: 15/116,642

(22) PCT Filed: Feb. 18, 2015

(86) PCT No.: PCT/IL2015/050190
§ 371 (c)(1),
(2) Date: Aug. 4, 2016

(87) PCT Pub. No.: WO2015/125143
PCT Pub. Date: Aug. 27, 2015

(65) Prior Publication Data
US 2016/0338615 A1    Nov. 24, 2016

Related U.S. Application Data

(60) Provisional application No. 61/942,366, filed on Feb. 20, 2014.

(51) Int. Cl.
*A61B 5/07* (2006.01)
*A61B 1/04* (2006.01)
*A61B 1/00* (2006.01)

(52) U.S. Cl.
CPC .......... *A61B 5/073* (2013.01); *A61B 1/00016* (2013.01); *A61B 1/041* (2013.01); *A61B 1/00036* (2013.01)

(58) Field of Classification Search
CPC ....... A61B 5/073; A61B 5/07; A61B 1/00011; A61B 1/00016; A61B 1/041; A61B 1/00036
(Continued)

(56) References Cited

U.S. PATENT DOCUMENTS 3,682,160 A * 8/1972 Murata ................ A61B 5/0031
331/117 R
5,604,531 A * 2/1997 Iddan ................ A61B 1/00016
348/76
(Continued)

FOREIGN PATENT DOCUMENTS

WO    WO 2008/038848    4/2008

*Primary Examiner* — Edwin Holloway, III
(74) *Attorney, Agent, or Firm* — Pearl Cohen Zedek Latzer Baratz LLP

(57) ABSTRACT

An in-vivo device includes a first communication circuit to communicate with an external communication device by using a first communication protocol while the in-vivo device is in the gastrointestinal system of a subject, a communication condition monitoring (CCM) circuit to monitor communication conditions for the first communication circuit, a second communication circuit to communicate with the external communication device by using a second communication protocol, and a controller configured to receive, from the communication condition monitoring (CCM) circuit, a signal indicative of a communication condition of the communication via the first communication circuit, to compare the communication condition to prerequisite communication condition(s), and to activate the first communication circuit and concurrently deactivate the second communication circuit, or vice versa, based on the comparison result.

15 Claims, 5 Drawing Sheets

(58) Field of Classification Search
USPC .......................................................... 340/3.1
See application file for complete search history.

(56) References Cited

U.S. PATENT DOCUMENTS

| | | | |
|---|---|---|---|
| 7,463,918 B2 | 12/2008 | Kim et al. | |
| 8,155,586 B2 | 4/2012 | Kim et al. | |
| 8,160,672 B2 | 4/2012 | Kim et al. | |
| 8,160,834 B2 * | 4/2012 | Liang | A61B 5/14532 |
| | | | 702/104 |
| 8,216,130 B2 | 7/2012 | Glukhovsky et al. | |
| 8,360,961 B2 | 1/2013 | Jung et al. | |
| 8,406,490 B2 | 3/2013 | Gat et al. | |
| 2004/0133089 A1 * | 7/2004 | Kilcoyne | A61B 1/00147 |
| | | | 600/350 |
| 2005/0177069 A1 * | 8/2005 | Takizawa | A61B 1/041 |
| | | | 600/573 |
| 2006/0030903 A1 * | 2/2006 | Seeberger | A61N 1/37223 |
| | | | 607/60 |
| 2006/0173265 A1 | 8/2006 | Kim et al. | |
| 2006/0243288 A1 * | 11/2006 | Kim | A61B 1/041 |
| | | | 128/899 |
| 2008/0193139 A1 | 8/2008 | Bettesh | |
| 2008/0288027 A1 * | 11/2008 | Kroll | A61B 5/0031 |
| | | | 607/60 |
| 2009/0182426 A1 * | 7/2009 | Von Arx | A61B 5/0031 |
| | | | 623/11.11 |
| 2009/0304093 A1 | 12/2009 | Shim et al. | |
| 2010/0022836 A1 * | 1/2010 | Colliou | A61B 5/0031 |
| | | | 600/118 |
| 2010/0130818 A1 | 5/2010 | Jung et al. | |
| 2010/0165088 A1 | 7/2010 | Seo | |
| 2010/0168517 A1 | 7/2010 | Shim et al. | |
| 2010/0179820 A1 * | 7/2010 | Harrison | G06F 19/3418 |
| | | | 705/2 |
| 2011/0286722 A1 | 11/2011 | Kim et al. | |
| 2012/0200318 A1 | 8/2012 | Shim et al. | |
| 2014/0003418 A1 | 1/2014 | Khait et al. | |

* cited by examiner

IN-VIVO DEVICE USING TWO COMMUNICATION MODES

CROSS-REFERENCE TO RELATED APPLICATIONS

This application is a National Phase application of PCT International Application No. PCT/IL2015/050190, entitled "IN-VIVO DEVICE USING TWO COMMUNICATION MODES" International Filing Date Feb. 18, 2015, published on Aug. 27, 2015 as International Publication No. WO 2015/125143, which in turn claims priority from U.S. Provisional Patent Application No. 61/942,366, filed Feb. 20, 2014, all of which are incorporated herein by reference in their entirety.

FIELD OF THE INVENTION

The present invention generally relates to communication between an in-vivo device (e.g., swallowable in-vivo device) and an external receiver or data recorder, and to a conditional selection of a communication method which is used by the in-vivo device and receiver (or data recorder).

BACKGROUND

In-vivo measuring systems and other types of in-vivo systems (e.g., in-vivo devices for performing surgical and the like operations) are known in the art. Some in-vivo devices/systems, which may traverse the gastrointestinal ("GI") system (mouth-to-anus), or other body organs/systems, may include an imaging sensor, or imager, for imaging (e.g., taking pictures of) the interior of the GI system. An in-vivo device may include one or more imagers and/or other sensors (e.g., pressure sensor, pH sensor, etc.). Other in-vivo devices may alternatively or additionally include a medication container and means for administering medication in the GI system. Other in-vivo devices may include means for performing surgical operations in vivo, and so on. Autonomous in-vivo devices are devices that traverse the GI system by being pushed in the GI system by peristaltic force exerted by the digestive system. Autonomous in-vivo devices may also spasmodically move in the intestinal tract in 'fits and starts'.

A swallowed in-vivo device may communicate with an external receiver. (When used herein "external" means in the subject but external to the swallowed in-vivo device, or external to the subject in which the swallowed device is located.) The external receiver may be worn by a subject in order to transfer images (and/or other sensory information) from the in-vivo device to the receiver, and, optionally, to transfer commands from the receiver to the in-vivo device, for example to change a mode of operation (e.g., a rate at which image frames are to be transmitted to the external receiver).

There are instances in which the communication between an in-vivo device and the external receiver is performed by using radio frequency ("RF") signals, and there are other instances in which the communication is performed by using non-RF techniques. Capsule type endoscopes made by Given Imaging, Israel, use RF communication means. Capsule type endoscopes made by Korea Institution of Science and Technology ("KIST"), Korea, includes a set of electrodes to communicate with an external receiver through contact (of the electrodes) with the subject's body.

RF communication between an in-vivo device and an external receiver is stated by KIST to have drawbacks. For example, according to KIST, since RF signals are used to transmit data, power consumption is large, thereby shortening operation time of the device, and reception sensitivity is worsened by, or deteriorated due to, electromagnetic interferences caused by various electronic appliances. In addition, KIST asserts that the circuit converting a video signal into a high frequency signal, and the antenna used for signal transmission, etc., increase the in-vivo device's real estate and production cost. KIST also asserts that using a high radio frequency may harm the human body.

Passing an electrical current through the body, as KIST does with its electrodes, may also pose some risks with respect to the human body though using that technique may enable faster data transfer (comparing to RF communication) to the external receiver. In the electrodes-based communication technique proposed by KIST the electrodes have to contact the body during communication in order to maintain communication continuity (e.g., avoid communication gaps). However, due to the capsule propagation nature (usually through peristalsis of the GI system) and environment in which the in-vivo device moves (the gastrointestinal system), communication gaps are likely to occur. Nevertheless, KIST does not seem to address the problem of communication gaps resulting from bad or unstable electrodes-body, contact or from complete loss of electrodes-body contact.

SUMMARY

Embodiments of the invention may transitionally use both techniques, such that one technique backs up the other, for example, during communication gaps in order to both improve communication continuity and benefit from both types of communication techniques.

An in-vivo sensing device (e.g., capsule like endoscope, in-vivo imaging sensor, etc.) may include a first communication circuit to communicate with a receiver external to the in-vivo device by using a first communication protocol while the in-vivo device is in the GI system of a subject, a communication condition monitoring ("CCM") circuit to continually monitor an electrical parameter characterizing, or associated with, the communication via the first communication circuit. For example, the electrical parameter may be an instantaneous electrical current ("IEC") consumed by the first communication circuit. ('Continually' means regardless of whether the first communication circuit is active or inactive; e.g., used or not.) The CCM may output (e.g., to a controller in the in-vivo device) a signal or data representative of the value of the monitored electrical parameter in order to (e.g., enable the controller to) compare actual communication conditions via the first communication circuit to a prerequisite communication condition(s) that are, for example, communication conditions that can sustain the communication. ('Prerequisite communication condition' is a minimal communication condition that still supports or facilitates gaps free communication between the two devices, or communication with low rate of communication gaps, in which case the low rate of gaps may be predetermined; e.g., may have or be associated with a gap's low-rate threshold.) The in-vivo sensing device may also include a second communication circuit as substitute (e.g., default) communication circuit, to facilitate communication with the receiver by using a second communication protocol.

The in-vivo device may further include a controller which may be configured to, for example, receive, from the CCM circuit, the signal or data representative of the electrical parameter representing or associated with the communication via the first communication circuit. The controller may determine, based on the instantaneous value, or state, of the electrical parameter, whether to activate the first communication circuit and concurrently or simultaneously deactivate the second communication circuit, or vice versa. For example, if the first communication circuit is active (i.e., used) (in which case the second communication circuit is inactive during that time) and the electrical parameter has a value, or it is in a state, indicating, confirming, or facilitating/supporting continuity of the communication between the first communication circuit and the external receiver (e.g., confirming that a communication condition of a communication via the first communication circuit complies with a prerequisite communication condition), the controller may refrain from interrupting communication via the first communication circuit. However, if the first communication circuit is active (in which case the second communication circuit is inactive during that time) and the (monitored) electrical parameter has a value indicating to the controller that the condition of the communication via the first communication circuit does not comply with a/the prerequisite communication condition (e.g., the controller interprets the value of the monitored parameter as indicating probable unacceptable communication gaps rate or gap(s) duration in the communication), the controller may temporarily transition communication from the first communication circuit to the second (backup) communication circuit (e.g., deactivate the first communication circuit and concurrently or simultaneously activate the second communication circuit). The controller may reactivate the first communication circuit (and deactivate the second communication circuit) when the monitored electrical parameter has a value, or state, that indicates an expected or required continuity of communication between the first communication circuit and the external receiver.

The first communication circuit and the second communication circuit are respectively referred to herein as primary communication circuit and auxiliary communication circuit.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

The description that follows provides various details of exemplary embodiments. However, this description is not intended to limit the scope of the claims but instead to explain various principles of the invention and the manner of practicing it.

Figure 1:
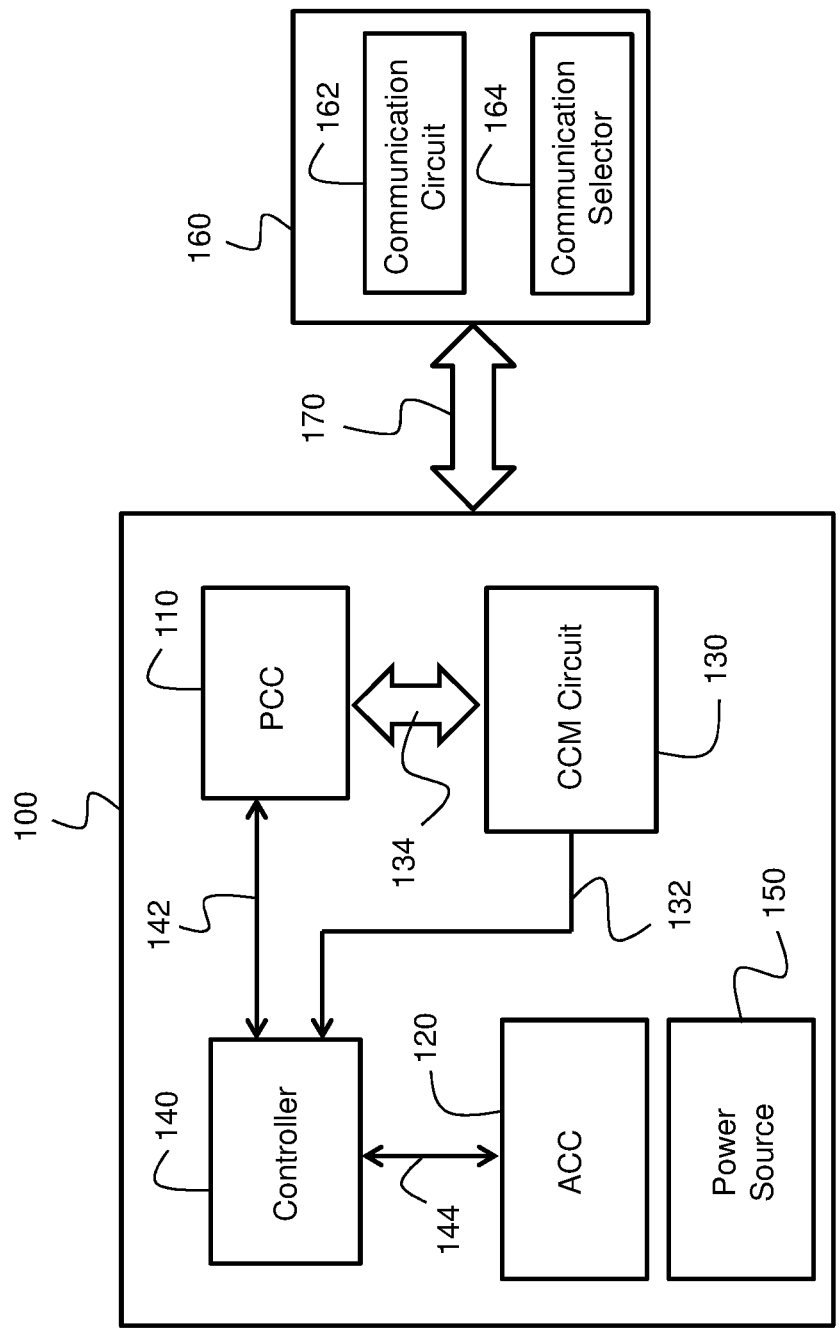
FIG. 1 shows a block diagram of an in-vivo device according to an example embodiment of the invention.

FIG. 1 is a block diagram of an in-vivo sensing device 100 according to an example embodiment of the invention. In-vivo sensing device 100 may include a first communication circuit 110, a second communication circuit 120, a communication condition monitoring (CCM) circuit 130, and a controller 140. In-vivo device 100 may include a power source (e.g., battery) 150 for powering in-vivo device 100. First communication circuit 110 is referred to herein as 'primary communication circuit' ("PCC"), and second communication circuit 120 is referred to herein as 'auxiliary communication circuit' ("ACC"). Controller 140 may be for example a computer processor and may be configured to carry our all or part of methods described herein by for example including dedicated circuitry and/or by executing instructions or software.

PCC 110 may facilitate communication between in-vivo sensing device 100 and an ex-vivo device 160 which is external to in-vivo sensing device 100, by using a first, or primary, communication protocol. ACC 120 may facilitate communication between in-vivo sensing device 100 and device 160 by using a second, or auxiliary, communication protocol. The first and second communication protocols may be different wireless protocols. For example, PCC 110 may use a baseband communication protocol and ACC 120 may use a modulation-based communication protocol. Alternatively, PCC 110 and ACC 120 may use different carrier frequencies and/or different modulation schemes to transfer data. In some embodiments device 160 may include two receivers. In other embodiments device 160 may include two receivers and two transmitters.

PCC 110 may include, for example, electrical electrodes to facilitate digital communication with ex-vivo device 160, and PCC 110 may use a communication protocol suitable for use with the electrical electrodes. For example, U.S. Pat. No. 8,160,672, to Korea Institute of Science and Technology (Korea), incorporated by reference herein, discloses a method for transmitting a signal from a sensor put in a human body to the outside of the human body by using transmitting electrodes. ACC 120 may include, for example, a RF circuit and a RF antenna to facilitate RF communication with receiver 160, and use a RF communication protocol suitable for communication, for example as disclosed by U.S. Pat. No. 5,604,531, to Given Imaging (Israel), incorporated by reference herein, which discloses an in-vivo device capable of transmitting data by using a modulator and radio frequencies.

Device 160 may include or use a communication circuit 162 that includes a first sub-circuit to facilitate communication with PCC 110, and a second sub-circuit to facilitate communication with ACC 120. Device 160 may also include a communication selector 164 to determine, in real time, which communication protocol is actually used by in-vivo sensing device 100 at any given time, and to select (i.e., activate) the sub-circuit of communication circuit 162 that matches (is suitable for) the communication protocol actually used by the in-vivo device.

Using the first communication protocol by PCC 110 may be preferable, in some instances, over, or have some benefits with respect to, the second communication protocol in terms of, for example, power consumption of power source 150, communication bandwidth, transmission rate, energy per transmitted bit, etc. However, if PCC 110 includes communication electrical electrodes that have to contact the subject's body to enable uninterrupted (i.e., steady) communication, this may render this communication technique susceptible to communication gaps because good contact between the electrodes and the subject's body, during the whole time the in-vivo device is in the subject's body, cannot be guaranteed, for example because of the erratic movement of the in-vivo device in the GI system. Therefore, it may be beneficial to communicate via PCC 110 as long as communication there through is satisfactorily performed or maintained, and to transition communication with device 160 to communication via ACC 120 every time a communication gap (interruption) is detected in the communication via PCC 110. In-vivo sensing device 100 may, therefore, conditionally communicate with device 160, over a communication path or medium 170, by using either PCC 110 or ACC 120. (The condition governing which communication circuit should be active or activated and which should be deactivated is described farther below.) The communication path or medium (170) may change according to the active communication circuit (e.g., PCC 110 or ACC 120). For example, the body of the subject swallowing the in-vivo device may embody, make or be part of the communication path or medium (170) if PCC 110 uses communication electrodes, and communication path or medium 170 may be an RF communication path/medium if ACC 120 uses RF communication antenna.

Transitioning of communication from PCC 110 to ACC 120, and vice versa, may be determined (e.g., by controller 140) based on a signal or data 132 that CCM 130 outputs, as described below. CCM 130 may monitor (134) an electrical parameter of PCC 110 (e.g., an electrical current, an electrical impedance, an electrical conductance, an electrical capacitance, etc.) while PCC 110 is active (e.g., when it communicates with device 160), and also during periods when PCC 110 is deactivated and ACC 120 is active (e.g., when it communicates with device 160). Signal/data 132 may represent a value or state such as an instantaneous value or state of the monitored electrical parameter.

CCM 130 may transfer signal/data 132 to controller 140, and controller 140 may, based on the value or state of the parameter indicated by signal/data 132, determine whether communication with device 160 via PCC 110 is satisfactory (e.g., 'sufficiently' sustained). If it is satisfactory, e.g., sufficiently sustained, controller 140 may refrain from transitioning between the two communication circuits (e.g., circuits 110 and 120). However, if controller 140 determines, based on the parameter's value or state, that communication with device 160 via PCC 110 has been compromised (e.g., disconnected)—for example if controller 140 has detected a gap in the communication via the PCC 110, whose temporal width and/or the rate of the communication gaps exceed a predetermined threshold value—controller 140 may transition communication (with device 160) from PCC 110 to ACC 120; namely, controller 140 may output a first control signal 142 to deactivate PCC 110, and, concurrently, at substantially the same time or in overlapping time, or simultaneously, a second control signal 144 to activate ACC 120.

CCM 130 may continue to monitor (134) the electrical parameter associated with PCC 110 after the communication transition occurs, while PCC 110 is deactivated (and while ACC 120 is active). Controller 140 may output signal 142 that activates PCC 110, and concurrently, at substantially the same time or in overlapping time, or simultaneously output signal 144 that deactivates ACC 120 when the parameter has a value, or state, that controller 140 may interpret as an indication that communication conditions via PCC 110 have sufficiently improved (e.g., they now, or again, satisfy a prerequisite communication condition) to sustain communication, at least for a while (e.g., per predetermined criteria), with device 160. In other words, controller 140 may use signal/data 132 to deactivate PCC 110 whenever communication conditions via PCC 110 are worsen or poor (e.g., they temporarily do not satisfy the prerequisite communication condition), and to reactivate PCC 110 if communication conditions improve and are acceptable to the extent that, based on continued monitoring, no interruptions seem to be imminent, at least not for a while.

Any of PCC 110 and ACC 120 may facilitate unidirectional communication or bidirectional communication with device 160. While unidirectional communication may include only transmission of sensory data (e.g., image data, pressure data, pH data, temperature data, etc.) from in-vivo device 100 to device 160 over communication path 170, bidirectional communication may also include transmission of data and/or commands from device 160 to in-vivo device 100, over communication path 170, for example to change a mode of operation, or state, of device 100.

Figure 2:
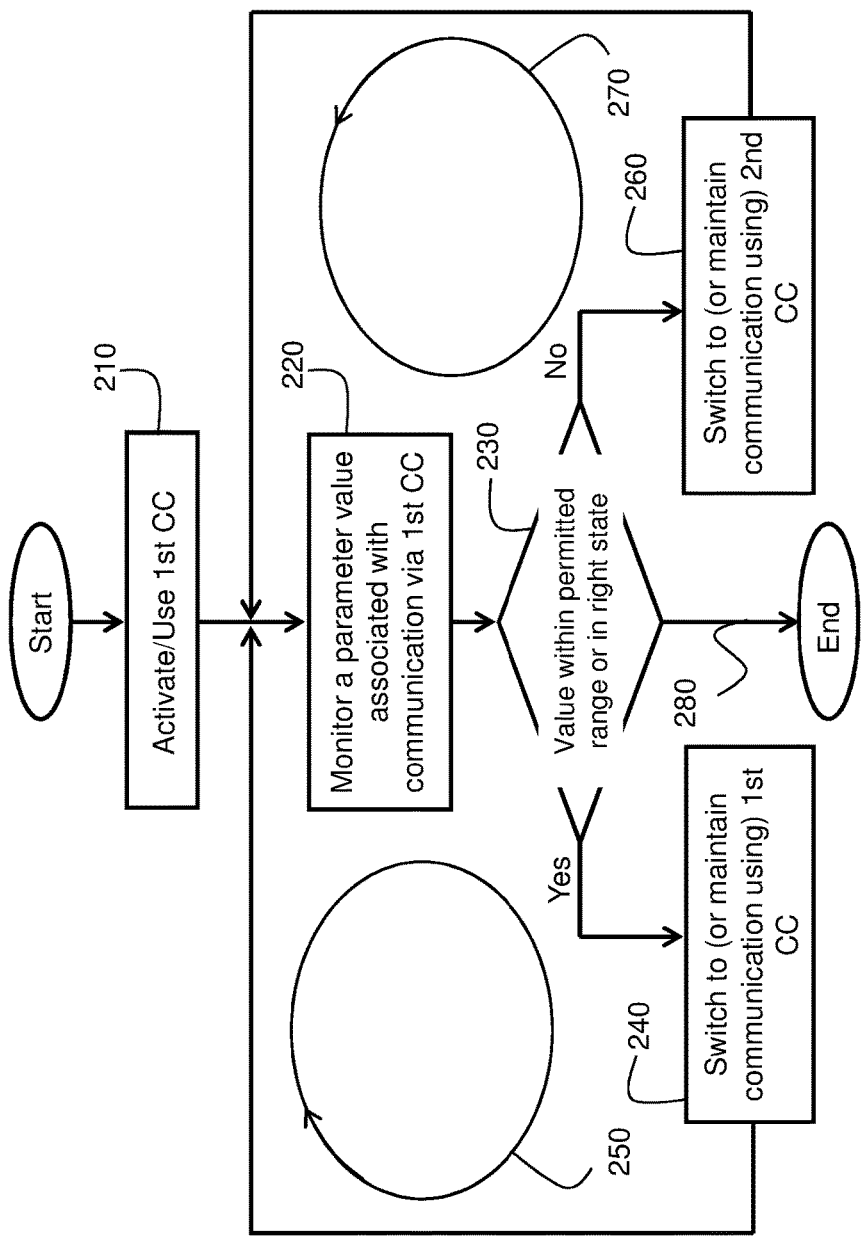
FIG. 2 shows a communication method according to an example embodiment of the invention.

FIG. 2 shows a communication method according to an example embodiment of the invention. FIG. 2 will be described in association with FIG. 1. At step 210, a controller of an in-vivo sensing device (e.g., controller 140 of device 100) may initially activate a first communication circuit ("CC") (e.g., PCC 110) as a default communication circuit, and concurrently, at substantially the same time or in overlapping time, or simultaneously deactivate, mute or shut down a second CC (e.g., ACC 120), to communicate with an external communication device or circuit (e.g., communication circuit 162) via the first CC, and the controller may continue to do so (maintain the state of the two CCs) if, or while, a value of a monitored electrical parameter, which is associated with the communication via the first CC, complies with a prerequisite communication condition.

The controller may use the first CC to, for example, transmit sensory information which in-vivo sensing device 100 may capture in vivo, such as images, pH information, pressure information, and, depending on the number and type of sensors of/in the in-vivo device, possibly additional or alternative information that the in-vivo sensing device may capture, sense or monitor in vivo. The controller may also use the first CC to receive information and/or commands from the external communication device.

At step 220, during the period of time when the in-vivo sensing device is in the body of a subject, a communication circuit monitoring circuit (e.g., CCM circuit 130) may monitor an electrical parameter associated with communication between the first CC and an external communication device (e.g., communication device 160) to thereby enable the controller to detect communication interruptions (e.g., electromagnetic interferences, communication gaps, etc.) in the communication between the first CC and the communication device, and, based on the value of the electrical parameter, to determine whether the communication condition(s) between the first CC and the external communication device is/are acceptable. If the value of the electrical parameter qualitatively, or quantitatively, indicates or suggests that communication condition(s) via the first CC is/are acceptable; that is, the value of the electrical parameter complies with prerequisite communication condition(s), communication via the first CC may continue. If the value of the electrical parameter qualitatively or quantitatively indicates or suggests that communication condition(s) via the first CC is/are unacceptable; that is, the value of the electrical parameter does not comply with the prerequisite communication condition(s), a communication circuit swap may take place; e.g., a transition from communication via the first CC to communication via the second CC may occur. (Communication interrupts may cause communication gaps during which transmitted data may be lost.) Communication, or potential communication, via the first CC is monitored (e.g., by monitoring the electrical parameter) regardless of whether the first CC is active or deactivated. That is, At step 230 controller 140 may check whether the value of the electrical parameter is within a permitted range (or whether the electrical parameter is at the 'right' state; e.g., the parameter has a value that is above a predetermined threshold value or below a predetermined threshold value), which is a range indicating, for example, good, reasonable or acceptable, communication conditions, or it exceeds the permitted range. If the value of the parameter is within the permitted range or at the correct/right state (shown as "Yes" at step 230), the controller may continue using, at step 240, the first CC; e.g., it may maintain or keep performing communication via the first CC. (The first CC may remain active while the second CC may remain deactivated.) Iteration loop 250 may reiterate or be repeated uninterruptedly as long as the value of the monitored electrical parameter remains within the permitted range or it is at the right state. (No communication circuit transitioning/swap occurs as long as (while) iteration loop 250 reiterates; the first CC may remain active and the second CC may remain non-active.)

If the value of the electrical parameter exceeds the permitted range, or it is in a 'wrong' state; e.g., below a predetermined threshold value or above a predetermined threshold value (shown as "No" at step 230), the controller may terminate iteration loop 250 and transition, at step 260, between the two communication circuits (e.g., between circuits 110 and 120); namely, it may deactivate the first CC and concurrently, at substantially the same time or in overlapping time, or simultaneously activate the second CC in order to resume communication between the in-vivo device (e.g., in-vivo sensing device 100) and the external communication device (e.g., device 160). The CCM circuit may, at step 220, monitor the electrical parameter associated with the communication with the external communication device via the first CC even during this transitional state during which the first CC is deactivated. Iteration loop 270 may reiterate uninterruptedly as long as the value of the monitored parameter exceeds the permitted range (or is at the wrong state). (While iteration loop 270 reiterates, no communication circuit transitioning/swap occurs; the second CC may remain active and the first CC may remain non-active.) However, if, per step 230, the monitored electrical parameter resumes or has a value which is within the permitted range (or it reverts to the right state), the controller (e.g., controller 140) may terminate iteration loop 270, deactivate the second CC and concurrently, at substantially the same time or in overlapping time, or simultaneously reactivate the first CC, at step 240, and recommence iteration loop 250, and so on.

Determining whether a parameter's value has to be above a predetermined threshold value or below a predetermined threshold value (optionally a different threshold value) in order to remain in a current communication mode (e.g., using the first CC or the second CC), or to transition between communication modes (e.g., from the first CC to the second CC, and vice versa), may depend on the type of the monitored electrical parameter. For example, the electrical parameter may be or it may represent, indicate, or be associated with electrodes-body tissue conductivity, signal-to-noise ratio, RF noise level, duration of communication gaps (individually or collectively), rate of communication gaps, sense electrical current or sense voltage (e.g., on a shunt component) that the first CC may use to sense communication condition(s), etc. The electrical parameter may indicate an electrical state of the first communication circuit. For example, the electrical state of the first communication circuit may refer to an electrical current or voltage measurable in the first CC or in connection with the activity of the first CC. Different electrical parameters may be used to determine transitioning of communication from the first CC to the second CC, and transitioning of communication from the second CC to the first CC. In embodiments in which the first CC uses electrical electrodes to transmit and/or receive data, all or some of the electrical electrodes may be monitored in order to evaluate or determine the communication condition of the communication via the first CC.

In some embodiments, transitioning from the first CC to the second CC may occur only if the value of the electrical parameter exceeds the permitted range (or if it is in the wrong state) for a predetermined time length. (By way of example, the time length may be a few milliseconds, say, 5 milliseconds.) Likewise, transitioning from the second CC to the first CC may occur only if the value of the electrical parameter is within the permitted range, or if it is in the right state, for a predetermined time length, which, by way of example, may be a few milliseconds (e.g., 7 milliseconds). (The two time lengths may be identical, or they may differ.)

When the in-vivo sensing device (e.g., device 100) exits the subject's body, the controller may shut down the entire device (100). The controller may detect exit of the in-vivo device from the subject's body in various ways, for example by sensing steady pressure, sensing temperature which is lower than the normal body temperature (37° C. or approximately 37° C.), inability to communicate with the external device (for example using the first CC or the second CC) for at least a certain amount of time (e.g., 20 minutes), etc.

Figure 3:
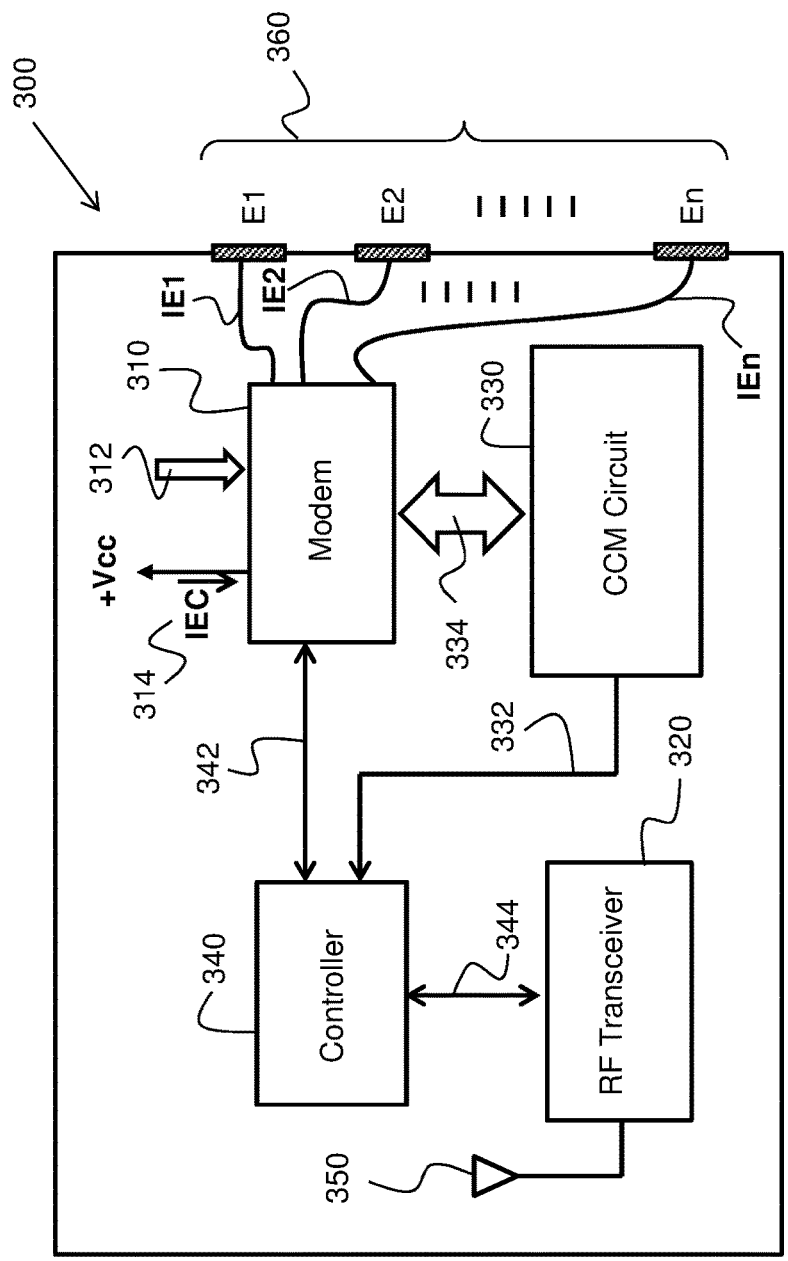
FIG. 3 shows an in-vivo device according to another example embodiment of the invention.

FIG. 3 shows an in-vivo sensing device 300 according to an example embodiment. In-vivo sensing device 300 may include a modem 310 as a primary communication circuit (PCC), a RF transceiver 320 as an auxiliary communication circuit (ACC), a communication condition monitoring (CCM) circuit 330, a controller 340 and a set of n electrical electrodes (360) which are designated as E1, E2, ..., En.

Modem 310 may have a data input 312 for receiving data. The data provided to modem 310 via data input 312 may be or include sensory data (e.g., image data) and other information (e.g., pressure information sensed in vivo). Modem 310 may communicate the data to an external device such as device 160 by transferring different voltage levels to electrodes E1-En, to thereby pass electrical current, or currents, between the electrodes via or through the body of the subject swallowing in-vivo device 300. In other words, electrodes E1-En and the subject's body jointly make up an electrical circuit which modem 310 may use to transfer digital data to an ex-vivo device (e.g., device 160). (The electrical currents respectively flowing through the electrodes may represent the data to be transferred.) The electrical currents generated between a pair, or pairs, of electrodes may remotely be sensed by an ex-vivo receiver via counter electrodes that may be attached to the subject's body (e.g., to her/his skin). (The external device, which may include communication electrodes, etc., is not shown in FIG. 3.)

Using modem 310 as a communication means may have advantages over RF transceiver 320. For example, modem 310 may facilitate faster data transfer to the ex-vivo device because modem 310, by using electrodes 360, may use a baseband based protocol. Modem 310 may be designed for two-way communication, in which case fast reception of commands from the ex-vivo device may be facilitated too. Another advantage of modem 310 may be lower power consumption comparing to the power consumption of RF transceiver 320. Electrodes E1, E2, ..., En, which are used by modem 310 to transfer data, and the counter electrodes, which are used by the ex-vivo device to receive the data, have to contact the subject's body during the entire communication period. However, good contact of the electrodes cannot be guaranteed in every region/part of the gastrointestinal tract the in-vivo sensing device may be at or in, and even in the same GI region, electrodes-body contact may occasionally be disrupted or even completely lost. That is, electrodes of electrodes E1-En, which participate in the communication, may touch the subject's body most of the time, but one or more of these electrodes may occasionally be detached from the body, which may result in temporary loss of communication (communication gap).

CCM circuit 330 may monitor the communication conditions existing between modem 310 and the ex-vivo device with which modem 310 operates (e.g., it may monitor the communication conditions, e.g., an electrical parameter representing a communication condition to which modem 310 is subjected) in order to enable controller 340 to determine whether or not communication circuits swap (from modem 310 to RF transceiver 320, or, if RF transceiver 320 is currently active/used, vice versa) is required. Controller 340 may activate one communication circuit (modem 310 or RF transceiver 320) and deactivate the other (RF transceiver 320 or modem 310), and reuse a previously used communication system or method, by executing steps of the swap/transition method shown in FIG. 2, or a similar method.

A value of an instantaneous electrical current (IEC, shown at 314) consumed by modem 310 may be a function of the number of electrical electrodes 360 that contact the subject's body, and/or a function of the degree of body contact of each electrode. The value of the IEC may change within some margin that may accommodate for, for example, a change in the type of the contacted body tissue and degree of contact (e.g., 'strong' contact, 'weak' contact and contact degrees between these extremes). According to some embodiments the more electrodes contact the subject's body and the better the contact, the higher the value of the IEC (314) consumed, or sensed, by modem 310. The IEC may be an example electrical parameter of modem 310 which is monitored by CCM 330. Other electrical parameters may be used. For example, impedance measureable between electrodes may be used as an electrical parameter because there is correlation between the degree of body contact of electrodes and the impedance between electrodes. (Electrodes may be used to measure impedance of body tissues as an indication to the degree of body contact.) If an electrode is completely detached from the subject's body, the IEC may have a (non-contact) value that exceeds the range of values that typically characterize various degrees of contact. (This may be more so when two or more electrodes do not contact the body.)

CCM circuit 330 may monitor the IEC and/or provide sense electrical voltages to electrodes E1, E2, . . . , En, to electrically monitor these electrodes, and respectively measure the resulting electrical currents IE1, IE2, . . . , IEn, and provide signal or data (332) to controller 340 that may represent the value of the IEC consumed by modem 310 at any given time or selected time(s), and/or the measured electrical currents IE1, IE2, . . . , IEn. (Electrical current IEC (314) may represent, or be equivalent to, the electrical currents IE1, IE2, . . . , IEn.) All electrodes E1, E2, . . . , En, or only selected ones, may electrically be monitored by CCM circuit 330 in order to evaluate or determine the communication condition via modem 310, which is an exemplary first communication circuit; that is, in order to evaluate or determine the communication condition existing between modem 310 and an external device similar to external device 160.

Controller 340 may receive (332) from CCM circuit 330 the data representative of the value of the IEC and/or of the measured electrode currents IE1, IE2, . . . , IEn, and evaluate, based on one or more of these values, the communication conditions to which modem 310 is subjected. Controller 340 may determine from the IEC's value, for example, whether the communication conditions are excellent, good, fair, poor, bad, or non-existent, and, in general, whether the communication conditions can sustain communication between modem 310 and the ex-vivo device, or not. If controller 340 determines that the conditions can sustain communication via modem 310, controller 340 may continue to use modem 310 (and deactivate RF transceiver 320), or (re)activate modem 310 (if modem 310 is currently deactivated) and deactivate RF transceiver 320 if RF transceiver 320 is currently active. If controller 340 determines that the conditions (temporarily) cannot sustain communication with the ex-vivo device via modem 310, controller 340 may deactivate modem 310 (or maintain it deactivated if it is already deactivated) and concurrently, at substantially the same time or in overlapping time, or simultaneously activate RF transceiver 320, or reactivate it, if RF transceiver 320 is currently deactivated. If the communication conditions via modem 310 are not good enough to sustain communication with the ex-vivo device, controller 340 may communicate with the ex-vivo device via RF transceiver 320, for example by using a RF antenna 350.

An external device (e.g., device 160) cooperating with in-vivo sensing device 300 may include, in addition to a modem and RF transceiver, a communication selector to enable synchronization between device 300 and the external device in terms of the communication protocol selected by device 300 for communication with the external device. The communication selector may be configured to detect when the in-vivo device communicates using an electrodes-based communication protocol (e.g., using modem 310 and through or via electrodes E1-En), and when it communicates using RF-based communication protocol (e.g., using RF transceiver 320 and through or via RF antenna 350). The communication selector may output a signal or data to a controller that, in response to the signal or data, may activate the corresponding on-board communication circuit (e.g., modem or RF transceiver) and deactivate the other on-board communication circuit (e.g., RF transceiver or modem). The communication selector may functionally be identical or similar to communication selector 164 of FIG. 1.

Figure 4:
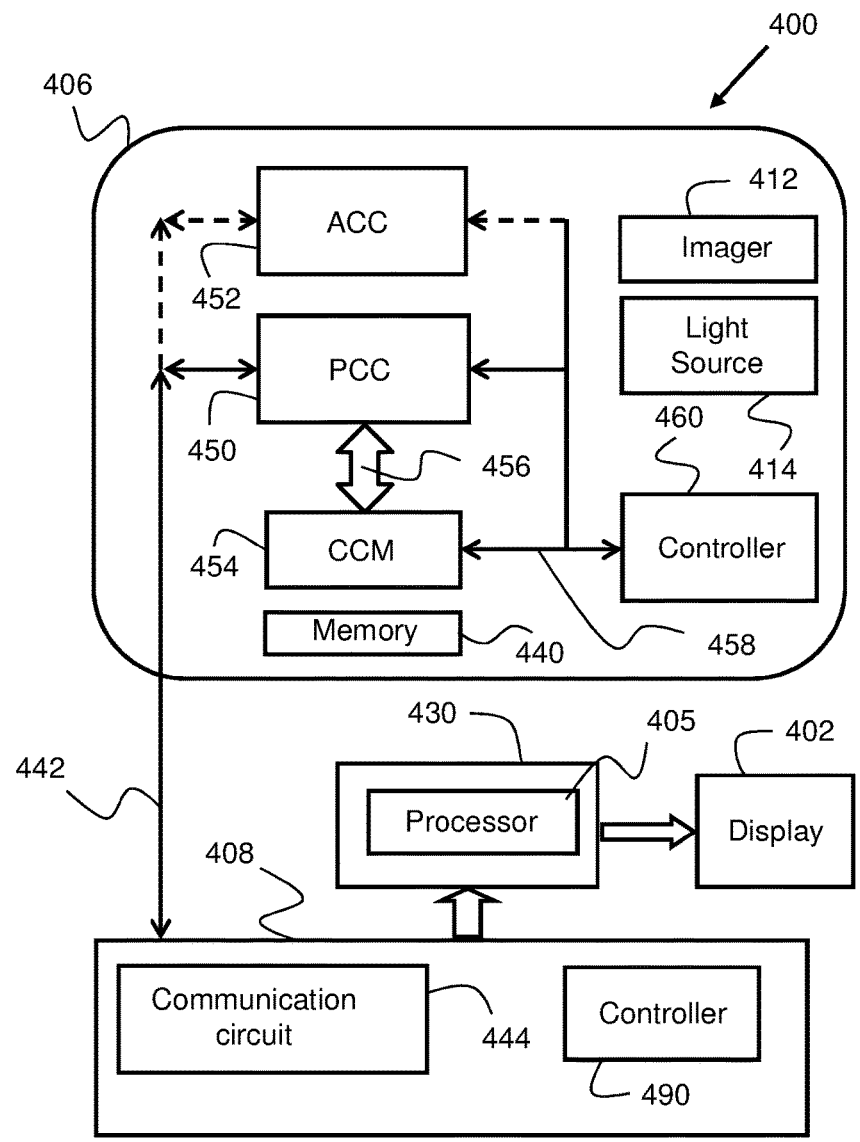
FIG. 4 shows an in-vivo system according to an example embodiment of the invention.

FIG. 4 shows an in-vivo imaging system 400 according to an example embodiment. In-vivo imaging system 400 may include an in-vivo device 406, a data recorder 408, a workstation 430, which may be, for example, a personal computer, and a display device 402 for displaying, for example, images, and for displaying various information related to the in-vivo device, etc. (Data recorder 408 is an example external communication device or circuit.) By way of example, in-vivo device 406 may include one imager (e.g., an imager 412), or more imagers. In-vivo device 406 may also include a light/illumination source 414 for illuminating a GI region, site or organ to be imaged, a controller 460, which may execute some or all of steps or procedure(s) executed, for example, by any of controller 140 and 340, or by both controllers, a memory 440 for storing data, a primary communication circuit (PCC) 450, an auxiliary communication circuit (ACC) 452 and a communication condition monitoring (CCM) circuit 454. PCC 450 and ACC 452 may be used (not simultaneously), for example by controller 460, to transmit (442) image frames (for example) and, optionally, to receive (442) data and/or commands from data recorder 408.

CCM circuit 454 may monitor (456) conditions of the communication via PCC 450 by monitoring an electrical parameter of PCC 450 (e.g., the instantaneous electrical current (IEC) consumed by PCC 450, impedance, etc.) which is correlated to (is a function of), and therefore provides indication to, or representing, the communication conditions via PCC 450. CCM 454 may output (458) to controller 460 a signal or data representative of a value or state of the electrical parameter (e.g., representative of the IEC). (Assume that PCC 450 is active and ACC is inactive.) Controller 460 may receive the signal/data transferred from CCM 454 and, based on the value (or state) of the electrical parameter, determine whether the communication conditions are good enough to sustain communication with data recorder 408 via PCC 450. ('Good enough' may mean there are no communication gaps, or there are communication gaps but the gaps are scarce or of short duration, for example per a predetermined threshold value.) If the communication conditions are good enough to sustain communication with data recorder 408 via PCC 450, controller 460 may maintain PCC 450 active and ACC inactive. If the communication conditions via PCC 450 imply that there is/are, for example too frequent or too long, communication gap(s), controller 460 may temporarily transition communication with device 408 from communication via PCC 450 to communication via ACC 452. ('Temporarily' means that communication via the PCC may be resumed as soon as the communication conditions permit it.) Controller 460 may resume communication via PCC 450 (and concurrently, at substantially the same time or in overlapping time, or simultaneously deactivate ACC 452) whenever controller 460 interprets the value (or state) of the electrical parameter as indicating that the prerequisite condition, or conditions, for communication via PCC 450 is/are satisfied; e.g., per predetermined criteria. Controller 460 may function in a similar way as controllers 140 and 340, and it may execute some or all the method steps shown in FIG. 2, or a similar method.

Data recorder 408 may include, for example, a communication circuit 444 and a controller 490. Communication circuit 444 may be configured to handle communication with both communication circuits 450 and 452, though in one embodiment not simultaneously. Data recorder 408 may include additional components for communicating with (e.g., transferring data frames, data, etc. to) a processing and/or displaying systems that may be configured to, for example, process images originating from in-vivo imager 412, localization data and related data. Workstation 430 may include a display or be functionally connected to an external display (402). Controller 490 of data recorder 408 may transfer data to workstation 430 for display on, for example, display 402.

Figure 5:
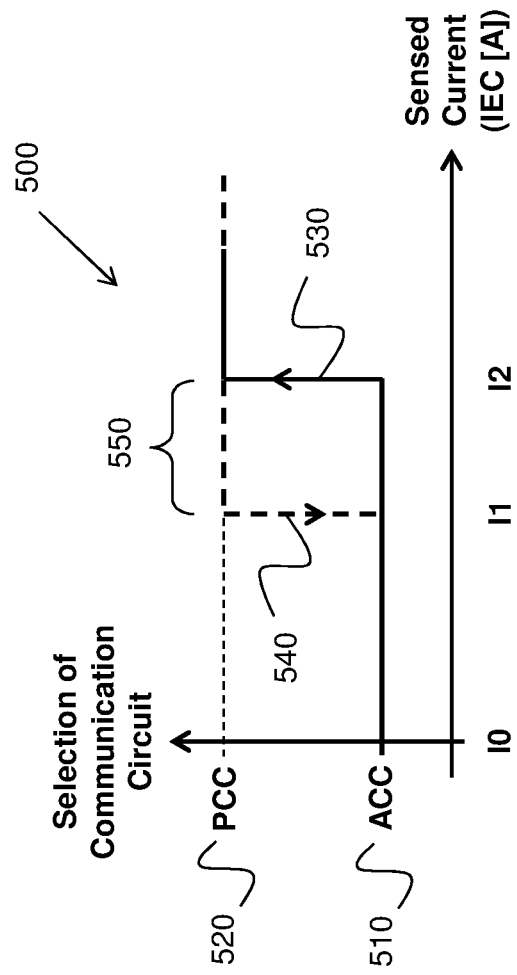
FIG. 5 shows a communication transition diagram according to an example embodiment.

FIG. 5 shows a communication circuit transitioning diagram 500 according to an example embodiment. Diagram 500 illustrates transitioning between communication via a first communication circuit (e.g., PCC) and communication via a second communication circuit (e.g., ACC) as a function of an electrical parameter representative of, or characterizing, a communication via the first communication circuit.

In diagram 500, the horizontal axis (abscissa) designates, by way of example, the value of an electrical current that a communication condition monitoring (CCM) circuit similar to CCM 130 or CCM 330 may sense when it monitors operation of a PCC similar to PCC 110 or PCC 310. The vertical axis (ordinate) indicates two operation states, 510 and 520, that respectively pertain to activation of two communication circuits ('ACC' state, shown at 510, and 'PCC' state, shown at 520) that may be selected by a device that uses these, or similar, circuits. The diagram of FIG. 5 shows how each communication circuit (ACC, PCC) may be selected for communication. FIG. 5 will be described in association with FIG. 1.

CCM 130 may continually monitor the instantaneous electrical current (IEC) consumed by PCC 110, and transfer to controller 140 a signal or data that represents the IEC. If the value of the IEC is within a range I0-I2 (I0 may be zero and I2, which is greater than T0, may be predetermined), controller 140 may determine that the communication conditions are not good enough to communicate with, for example, ex-vivo device 160 via PCC 110 (i.e., the communication conditions do not satisfy a prerequisite condition related to the communication via PCC 110). Therefore, controller 140 may select ACC 120 (the selection is shown at 510) as the communication means (instead of PCC 110). If the value of the IEC is greater than I2, controller 140 may determine that the communication conditions have improved enough to sustain communication with ex-vivo device 160 via PCC 110. Therefore, controller 140 may transition (530) from the ACC state (510) to the PCC state (520); that is, controller 140 may deselect/deactivate ACC 120 and, instead, select/activate PCC 110 as the communication means.

Controller 140 may keep monitoring (e.g., via CCM 130) the communication conditions of/via PCC 110 while PCC 110 is in operation (e.g., selected as the communication means) and continue operating PCC 110 if the value of the IEC associated with PCC 110 remains greater than I2. However, if the value of the IEC becomes less than I1 (0<I1<I2; I1 may also be predetermined), controller 140 may transition (540) from the PCC state (520) to the ACC state (510); that is, controller 140 may deselect/deactivate PCC 110 and, instead, reselect/reactivate ACC 120 as the communication means. The margin (difference) 550 (hysteresis width 1241), prevents jitters in the transitions from PCC 110 to ACC 120, and vice versa.

A change in the value of the IEC with respect to the predetermined current values I1 and I2 may not suffice to effect a transition. That is, if a new value of the IEC increases passed I2, it has to remain greater than I2 for at least a predetermined time period (e.g., at least for a few milliseconds) in order for controller 140 to determine that a transition can take place. Likewise, if a new value of the IEC decreases passed I1, it has to remain less than I1 for at least a predetermined time period (e.g., at least for a few milliseconds) in order for controller 140 to determine that the opposite transition can take place.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not constrained to a particular order or sequence of steps, operations or procedures. Additionally, some of the described method embodiments or elements thereof can occur or be performed at the same point in time.

The articles "a" and "an" are used herein to refer to one or to more than one (e.g., to at least one) of the grammatical object of the article, depending on the context. By way of example, depending on the context, an "element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as memory 440 and a controller such as controller 140, 340, or 460. Some embodiments may be provided in a computer program product that may include a non-transitory machine-readable medium, having stored thereon instructions, which may be used to program a computer, or other programmable devices, to perform methods as disclosed above. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of in-vivo devices (e.g., in-vivo devices with one or more imagers, in-vivo devices with no imagers at all, etc.), and to various types of communication schemes and protocols. Hence the scope of the claims that follow is not limited by the disclosure herein.

The invention claimed is:

1. An in-vivo device comprising:
a first communication circuit to communicate with a receiver external to the in-vivo device by contacting of one or more electrodes with the body of a subject using a first communication protocol while the in-vivo device is in the gastrointestinal system of the subject;
a communication condition monitoring circuit to monitor an electrical parameter associated with communication via the first communication circuit, the electrical parameter selected from the group consisting of: an electrical current consumed by the first communication circuit; electrodes-body tissue conductivity; electrical impedance; electrical conductance; and rate of communication gaps, and to output a signal representative of a value of the monitored electrical parameter;
a second communication circuit to communicate with the receiver by using a second communication protocol; and
a controller to receive the signal from the communication condition monitoring circuit, and to activate the first communication circuit and concurrently deactivate the second communication circuit, or vice versa, based on the value of the electrical parameter.

2. The in-vivo device as in claim 1, wherein the controller is configured to activate the first communication circuit and to concurrently deactivate the second communication circuit if a communication condition represented by the value of the electrical parameter complies with a prerequisite communication condition.

3. The in-vivo device as in claim 1, wherein the controller is configured to deactivate the first communication circuit and to concurrently activate the second communication circuit if a communication condition represented by the value of the electrical parameter does not comply with a prerequisite communication condition.

4. The in-vivo device as in claim 3, wherein the controller is further configured to resume communication via the first communication circuit if, during communication via the second communication circuit, the communication condition via the first communication circuit complies with the prerequisite communication condition.

5. The in-vivo device as in claim 1, wherein the second communication circuit comprises a radio frequency circuit.

6. The in-vivo device as in claim 1, wherein the electrical parameter indicates an electrical state of the first communication circuit.

7. A communication method for an in-vivo system, comprising:
in an in-vivo device comprising a controller, a first communication circuit to communicate with an external communication circuit external to the in-vivo device by contacting of one or more electrodes with the body of a subject, a second communication circuit and a communication condition monitoring circuit, performing,
receiving by the controller, from the communication condition monitoring circuit, a signal indicative of an electrical parameter associated with communication between said first communication circuit and the external communication circuit, the electrical parameter selected from the group consisting of: an electrical current consumed by the first communication circuit; electrodes-body tissue conductivity; electrical impedance; electrical conductance; and rate of communication gaps; and
activating, by the controller, the first communication circuit and concurrently deactivating the second communication circuit, or vice versa, depending on a value or state of the electrical parameter.

8. The method as in claim 7, comprising initially activating the first communication circuit and concurrently deactivating the second communication circuit, and continuing to do so if, or while, the value of the electrical parameter complies with a prerequisite communication condition.

9. The method as in claim 7, comprising activating the second communication circuit and concurrently deactivating the first communication circuit if the value of the electrical parameter does not comply with a prerequisite communication condition.

10. The method as in claim 9, comprising resuming communication via the first communication circuit if, during communication via the second communication circuit, the value of the electrical parameter complies with the prerequisite communication condition.

11. The method as in claim 9, wherein transitioning of communication from the first communication circuit to the second communication circuit and transitioning of communication from the second communication circuit to the first communication circuit involves using different electrical parameters.

12. A communication method for an in-vivo system, comprising:
   (i) activating a first communication circuit in an in-vivo device to communicate with an external communication device by contacting of one or more electrodes with the body of a subject while the in-vivo device is in the gastrointestinal system of a subject, and monitoring a communication condition of the communication via the first communication circuit; and
   (ii) deactivating the first communication circuit and concurrently activating a second communication circuit in the in-vivo device to maintain communication with the external communication device if the communication condition does not comply with a prerequisite communication condition, the communication condition selected from the group consisting of: an electrical current consumed by the first communication circuit; electrodes-body tissue conductivity; electrical impedance; electrical conductance; and rate of communication gaps.

13. The method as in claim 12, comprising:
   (iii) reactivating the first communication circuit and concurrently deactivating the second communication circuit if, during communication via the second communication circuit, the communication condition via the first communication circuit, complies with the prerequisite communication condition; and
   (iv) repeating steps (ii) and (iii) while the in-vivo device is in the gastrointestinal tract.

14. The method as in claim 12, wherein operating the second communication circuit comprises using a radio frequency (RF) circuit.

15. The method as in claim 12, comprising monitoring all or some of the electrical electrodes to evaluate the communication condition of the communication via the first communication circuit.

* * * * *